United States Patent
Maxon-Maldonado

(10) Patent No.: US 8,485,995 B1
(45) Date of Patent: Jul. 16, 2013

(54) SYSTEM AND METHOD FOR THERMAL COMPRESSION THERAPY

(75) Inventor: Gregory Brian Maxon-Maldonado, Phoenix, AZ (US)

(73) Assignee: Maldonado Medical LLC, Phoenix, AZ (US)

(*) Notice: Subject to any disclaimer, the term of this patent is extended or adjusted under 35 U.S.C. 154(b) by 739 days.

(21) Appl. No.: 12/501,258

(22) Filed: Jul. 10, 2009

Related U.S. Application Data

(60) Provisional application No. 61/134,676, filed on Jul. 10, 2008, provisional application No. 61/134,677, filed on Jul. 10, 2008.

(51) Int. Cl.
*A61H 1/00* (2006.01)

(52) U.S. Cl.
USPC ............... 601/15; 601/84; 601/148

(58) Field of Classification Search
USPC ................. 601/15, 148–152, 84
See application file for complete search history.

(56) References Cited

U.S. PATENT DOCUMENTS

| | | | |
|---|---|---|---|
| 5,329,751 A | 7/1994 | Wadsworth | |
| 5,624,188 A | 4/1997 | West | |
| 5,634,890 A | 6/1997 | Morris | |
| 5,989,285 A | 11/1999 | Devilbiss et al. | |
| 6,855,158 B2 | 2/2005 | Stolpmann | |
| 7,591,796 B1 * | 9/2009 | Barak et al. | 601/152 |
| 7,871,387 B2 | 1/2011 | Tordella et al. | |
| 7,931,606 B2 | 4/2011 | Meyer | |
| 8,029,451 B2 | 10/2011 | Meyer et al. | |
| 8,100,956 B2 | 1/2012 | Quisenberry et al. | |
| 8,128,672 B2 | 3/2012 | Quisenberry et al. | |
| 8,142,486 B2 | 3/2012 | Quisenberry et al. | |
| D662,212 S | 6/2012 | Quisenberry | |
| D662,213 S | 6/2012 | Quisenberry | |
| D662,214 S | 6/2012 | Quisenberry | |
| D664,260 S | 7/2012 | Quisenberry | |
| 2004/0158285 A1 * | 8/2004 | Pillai | 606/204 |
| 2005/0143797 A1 | 6/2005 | Parish et al. | |
| 2006/0189907 A1 | 8/2006 | Pick et al. | |
| 2008/0058911 A1 | 3/2008 | Parish et al. | |
| 2008/0132816 A1 | 6/2008 | Kane et al. | |
| 2009/0069731 A1 * | 3/2009 | Parish et al. | 601/150 |
| 2010/0210982 A1 | 8/2010 | Balachandran et al. | |
| 2011/0077723 A1 | 3/2011 | Parish et al. | |
| 2011/0275983 A1 | 11/2011 | Quisenberry et al. | |
| 2012/0191031 A1 | 7/2012 | Quisenberry | |

FOREIGN PATENT DOCUMENTS

| | | |
|---|---|---|
| WO | 2005007060 | 1/2005 |
| WO | 2007120639 | 10/2007 |
| WO | 2008051417 | 5/2008 |

OTHER PUBLICATIONS

Office Action dated Jun. 6, 2012 in U.S. Appl. No. 12/501,269.
Office Action dated Jun. 12, 2012 in U.S. Appl. No. 12/501,275.
Office Action Restriction dated Apr. 26, 2012 in U.S. Appl. No. 12/501,275.
Office Action dated Nov. 20, 2012 in U.S. Appl. No. 12/501,369.
Final Office Action dated Sep. 28, 2012 in U.S. Appl. No. 12/501,275.
Advisory Action dated Dec. 28, 2013 in U.S. Appl. No. 12/501,275.
Office Action dated Feb. 6, 2013 in U.S. Appl. No. 12/234,394.

* cited by examiner

*Primary Examiner* — Michael A. Brown
(74) *Attorney, Agent, or Firm* — Snell & Wilmer L.L.P.

(57) ABSTRACT

A method for providing a combined DVT and compression therapy to a patient is provided. The method includes providing a control unit configured to condition heat transfer fluid and to selectively provide a compressed gas, providing a thermal compression device that is mountable to a select portion of the patient, and programming the control unit to supply heat transfer fluid to the thermal compression device and to supply compressed gas to the thermal compression device.

18 Claims, 7 Drawing Sheets

SYSTEM AND METHOD FOR THERMAL COMPRESSION THERAPY

CONTINUITY DATA

This application claims priority to and the benefit of U.S. Provisional Application Ser. No. 61/134,677, filed on Jul. 10, 2008, and U.S. Provisional Application Ser. No. 61/134,676, filed on Jul. 10, 2008, both of which are incorporated herein in their entirety.

FIELD OF THE INVENTION

A medical device and therapy system is presented. More particularly, an apparatus and system for providing combined heating or cooling and compression therapy is presented for use, by way of general example, in reducing edema and pain and preventing deep vein thrombosis (DVT).

BACKGROUND OF THE INVENTION

Various medical devices have been developed to deliver warming therapy and cooling therapy to patients recovering from injuries or surgeries. Additionally, it is known to provide a pressurized massage therapy, sometimes referred to as external pneumatic compression ("EPC"), to these patients. Typical recipients of these therapies are patients recovering from orthopedic surgeries or injuries to various areas of the anatomy, particularly legs and knee and shoulder joints. A cooling therapy, heating therapy, and compression therapy can also be combined with a motion therapy in which a patient's joint is carefully and slowly moved through its natural motion so as to maintain flexibility in the joint. The above-described therapies have proven useful in speeding recovery and avoiding deleterious impacts of deep vein thrombosis among other benefits.

In typical therapeutic arrangements an external control device provides a mechanical pumping and circulation force as well as an automated control of the pneumatic forces. Fluids from the control device are passed through flexible tubes which are then directed to a core to be wrapped around the area to receive therapy. In this manner heated fluids, chilled fluids, and/or air pressure can be administered to the injured area when the core is applied to or wrapped around the patient's body. Arrangements of this type are described in U.S. Pat. No. 5,989,285; and US Published Patent Application Publication No. 2008/0058911, both of which are incorporated herein by reference to describe the general level of knowledge held by persons skilled in the art.

Nevertheless, the systems and methods described in the prior art continue to suffer from various shortcomings and are in need of improvement. One such shortcoming relates to the high cost associated with the core portion of the thermal compression therapy apparatus. The core portion, that portion of the apparatus that is wrapped around an area of the patient's body (a knee joint for example) is generally an expensive item. It comprises various tubings and channels that distribute the fluids through the core so that they will surround the area to be treated. However, the core necessarily comes into contact with the patient. Thus, the core can easily become contaminated with blood and other discharges and fluids emitted by the recovering patient. Also, good hygiene practices also call for the sterilization of each core after a treatment if the core is to be reused. However, given the somewhat delicate nature of the materials and structures contained within the core a sterilization process is not effective. Given the cost of the core, throwing each core away after a single use is an expensive option. Thus, it would be desired to find a way to easily reuse cores so that a single core can be used multiple times before it needs to be discarded.

Further, the core structure itself suffers from various limitations in the present design and is in need of improvement. As previously described, a patient's joint, for example the knee joint, can be gradually flexed during a treatment. This movement of the joint necessarily flexes the core that is wrapped around the joint. During such therapies there is a tendency within the core to fold and obstruct portions of the core that is repeatedly being bent. The cores can then suffer from malfunction or poor performance (even distribution of fluids) as various tubings are obstructed. There exists a need to overcome this shortcoming in current core designs.

An additional need for improvement relates to the heating and cooling therapy applied to the patient. In current methods there is no direct way to determine the skin temperature of the patient in that area where the patient is receiving therapy. The skin is typically covered by the core. However, that is an important item of data to assure that the patient's body is not being overheated (burned) or overly chilled (frost bitten). Elderly patients or patients with severe trauma may suffer from an inability to sense temperature extremes; thus it falls upon the attending technician, nurse, or other professional to maintain a proper temperature. While the temperature exiting from the control machine can sometimes be programmed there is needed a way to confirm that the temperature at the patient also corresponds to that temperature. Hence, it would be desired to provide a core that enables a quick, easy, and reliable detection and confirmation of the patient's skin temperature where covered by the core.

Hence there has been identified a need to provide an improved therapy core and related system for providing warming therapy, cooling therapy, and compression therapy. It would be desired that the improved system or apparatus allow for multiple uses. It would further be desired that the improved system or apparatus provide an improved function, both with relation to fluid distribution and with respect to temperature detection. Further, there is a need that the improved Thermal compression therapy apparatus and system be adapted for use with present controllers and pneumatic devices. Finally, there is a need for an improved therapy core to provide a robust and strong performance while at the same time providing cost advantages over presently known systems and methods.

SUMMARY

An apparatus and system for compression and thermal therapy is presented. In a first aspect of, by way of example only, a combined heating, cooling, and compression therapy system is provided. The system is configured for automated use with a controller. The therapy system is also particularly designed for easy use with multiple patients. The therapy system comprises a reusable core through which a separate compression apparatus and a heating/cooling apparatus are positioned. The core can be placed in a disposable outer cover. The disposable cover is typically the outer portion of the system that would come into contact with a patient's body. Thus, the outer cover can comprise an impermeable layer such that blood and other bodily fluids cannot pass through the cover and contact the core. In one aspect, the outer cover comprises an opening such that the core can be easily passed through the opening and into an interior volume of the cover, and the interior volume of the cover is designed to closely hold the core in a desired position. The outer cover, which comes into contact with the patient, can comprise a temperature nodule attached to a surface for monitoring the temperature of the patient's skin. When a treatment session is completed, the core can be removed (and later reused), and the outer cover can be disposed.

In accordance with a further aspect, and still by way of example only, there is provided an improved therapeutic system for providing a combination of compression therapy and cold and heat therapy. The system comprises a core having two separate channels for providing cold and heat and compression therapy; a cover for receiving the core; and a skin sensitive temperature node attached to the core cover. The therapy system can further be configured such that the cover defines an interior volume and an exterior region. The cover comprises an opening such that the core can be positioned within the interior volume of the cover by passing through the opening. Further, the cover can comprise a hook and loop attachment means (Velcro® type fastener) disposed proximate to the opening and configured to permit the opening to be opened and closed. The temperature node measures skin temperature as by way of a thermometer or thermocouple. In one aspect a visual color coded thermometer is used.

Other independent features and advantages of the Thermal compression therapy apparatus and system will become apparent from the following detailed description, taken in conjunction with the accompanying drawings which illustrate, by way of example, the principles of the invention.

DETAILED DESCRIPTION OF THE FIGURES

These and other features of the invention will become more apparent in the detailed description in which reference is made to the appended drawings wherein.

DETAILED DESCRIPTION OF THE INVENTION

The present invention can be understood more readily by reference to the following detailed description, examples, drawing, and claims, and their previous and following description. However, before the present devices, systems, and/or methods are disclosed and described, it is to be understood that this invention is not limited to the specific devices, systems, and/or methods disclosed unless otherwise specified, as such can, of course, vary. It is also to be understood that the terminology used herein is for the purpose of describing particular aspects only and is not intended to be limiting.

The following description of the invention is provided as an enabling teaching of the invention in its best, currently known aspect. To this end, those skilled in the relevant art will recognize and appreciate that many changes can be made to the various aspects of the invention described herein, while still obtaining the beneficial results of the present invention. It will also be apparent that some of the desired benefits of the present invention can be obtained by selecting some of the features of the present invention without utilizing other features. Accordingly, those who work in the art will recognize that many modifications and adaptations to the present invention are possible and can even be desirable in certain circumstances and are a part of the present invention. Thus, the following description is provided as illustrative of the principles of the present invention and not in limitation thereof.

As used throughout, the singular forms "a," "an" and "the" include plural referents unless the context clearly dictates otherwise. Thus, for example, reference to "a core" can include two or more such cores unless the context indicates otherwise.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

As used herein, the terms "optional" or "optionally" mean that the subsequently described event or circumstance may or may not occur, and that the description includes instances where said event or circumstance occurs and instances where it does not.

Figure 1:
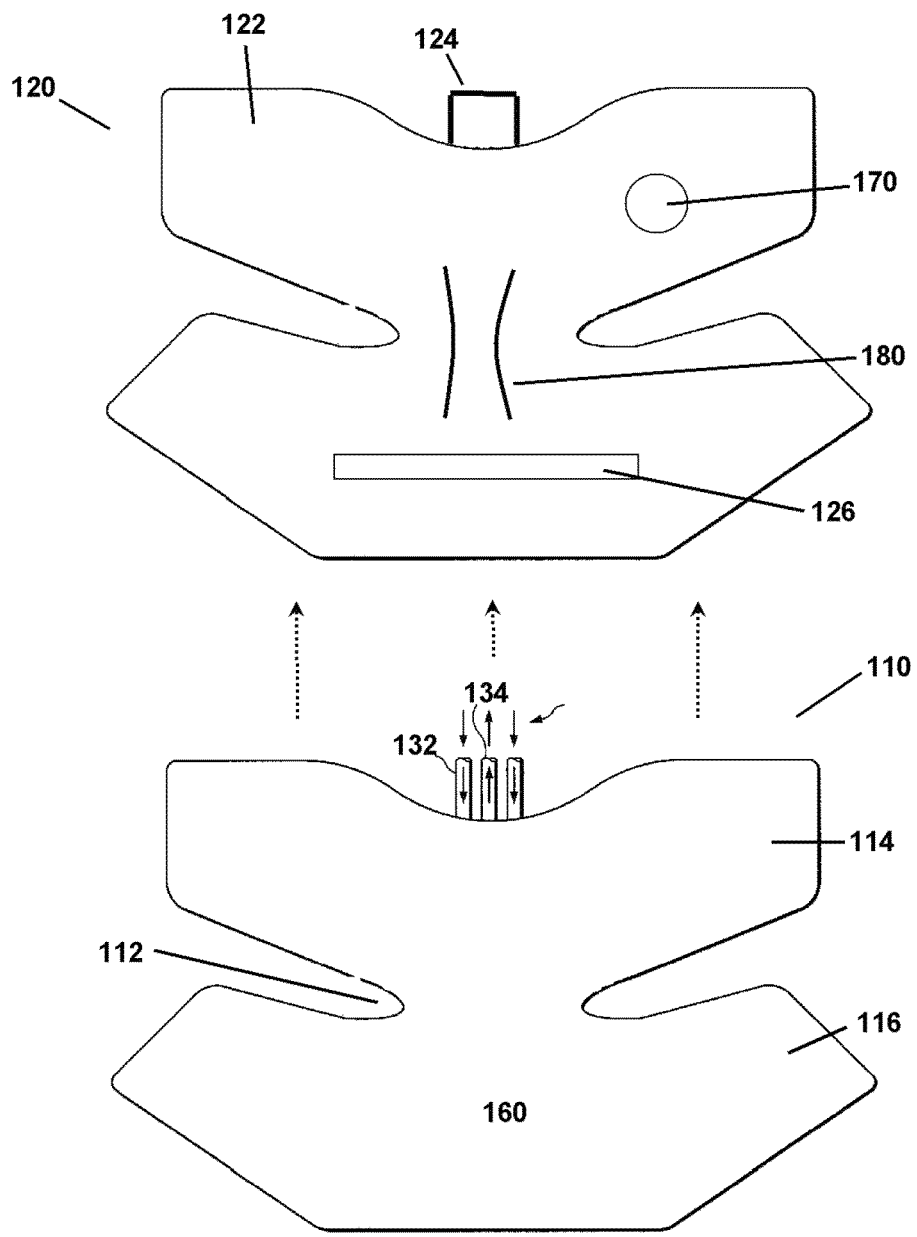
FIG. 1 is overhead plan view one aspect of a thermal compression therapy unit adapted for use with a patient's knee, showing a cover and a core configured for receipt by the cover.

Referring now to FIG. 1, one aspect of a combined thermal compression therapy apparatus or system is presented. The thermal compression unit comprises a core 110 and cover 120. While the core 110 and cover are shown in an exploded arrangement in FIG. 1, in usage, the core can be assembled with the cover 120 as explained further herein. The core comprises at least one first channel 130 and at least one second channel. The channels 130, 140 can be connected by tubing 150. Generally, the cover defines an interior volume 160 for receiving the core and an exterior region 122. In one aspect, the exterior region 122 of the cover comprises an impermeable surface which is generally the surface of the cover that comes into contact with a patient.

As would be understood by a person skilled in the art, liquid tubing and gas (or air) tubing can be connected to a supply machine or control unit 200 that supplies liquid and gas materials to the core via the tubing 150. In the case of liquid tubing, a fluid can be heated or chilled to a desired temperature. In one aspect, the fluid comprises distilled water, and can also comprise distilled water and alcohol. This fluid is then directed through liquid tubing (typically having both an inlet and an outlet tubing) so as to circulate the fluid through the channels and thereby to provide heating or chilling therapy to a patient. The channels 130, 140 can comprise a series of baffles or other flow directing structures to distribute the fluid to the desired zones or sections of the core 110. In one aspect, a wide distribution of fluid is provided to avoid significant temperature gradients between one section or area of the core to another. In addition, gas tubing can receive a gas fluid (such as air) also directed from the supply machine or control unit 200. A separate network of channels distributes gas through the core. The pressure of the gas can be controlled and varied so as to provide a rhythmic pulsing of pressure around the patient's body where the core is positioned. Thus, for example, in the treatment of a knee, the rhythmic cycling of gas pressure increases and decreases the air pressure in the core 110 around the knee to assist with circulation among other desired benefits. Thus, it will be appreciated that the gas network of channels can be separate from the liquid network of channels in the core so that each material provides its function; the liquid provides temperature therapy and the gas provides a pressure therapy. While all this is going on, the patient's body, such as a knee, can also be receiving a motion therapy, such as rhythmically straightening and flexing the knee joint. Thus, thermal compression units can be configured so as not to interfere with any possible flexion therapy. Additionally, while the aspects described above include providing pressure using compressed gas, it is also contemplated that other substances could be used to provide the desired compression.

Figure 2:
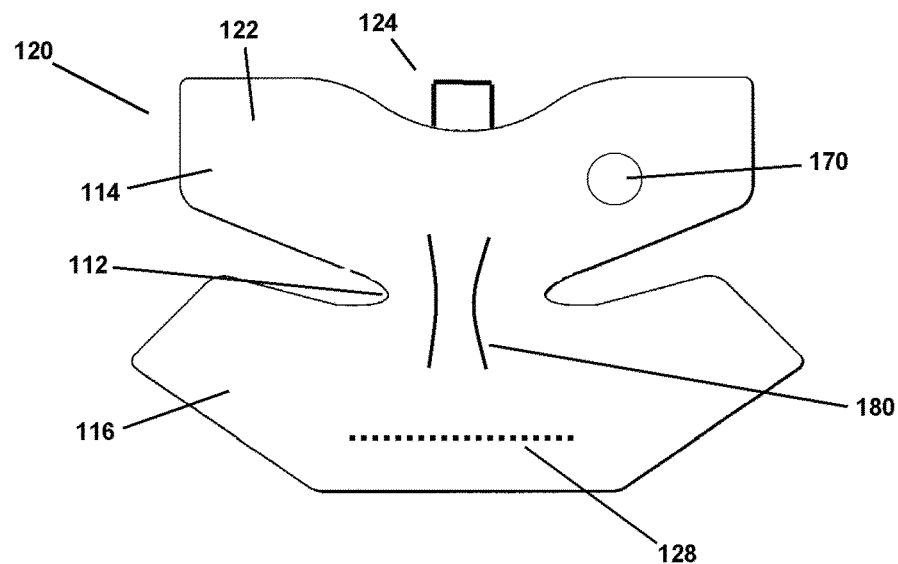
FIG. 2 is an overhead plan view of the cover of FIG. 1, illustrating a closing means.
Figure 3:
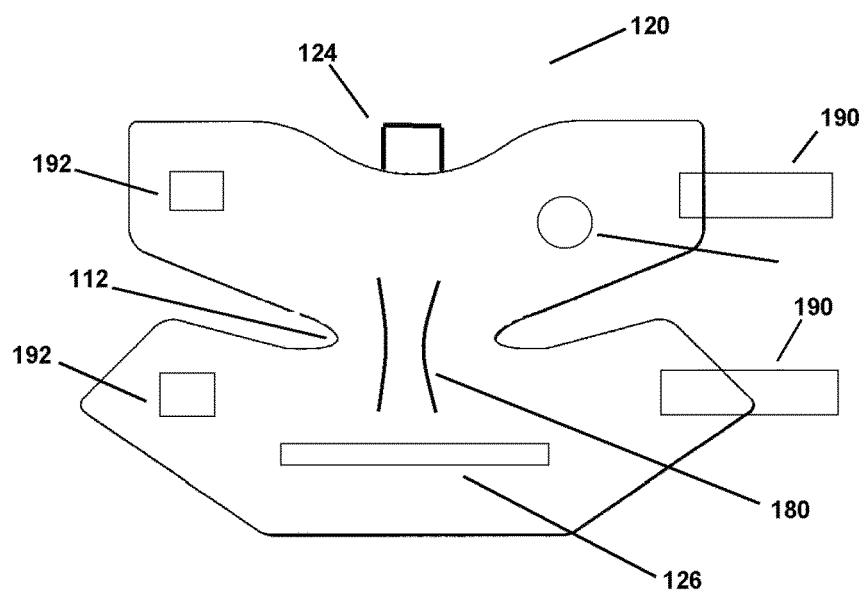
FIG. 3 is an overhead plan view of the cover of FIG. 1, illustrating straps and receiving areas.
Figure 4:
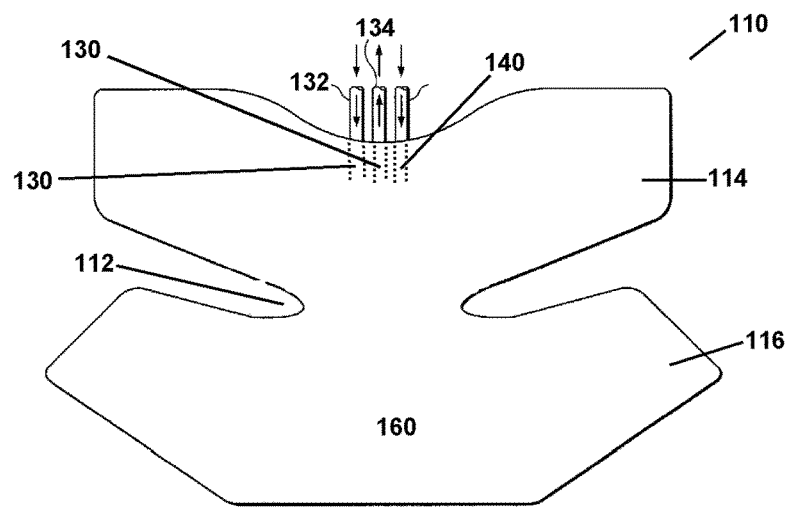
FIG. 4 is an overhead plan view of the core of FIG. 1.
Figure 5:
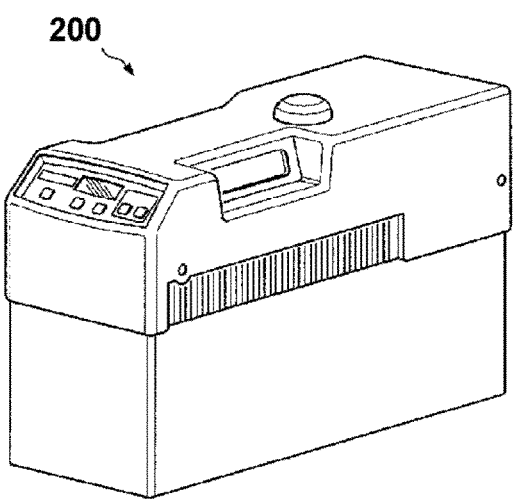
FIG. 5 is a front perspective view of one embodiment of a control unit.
Figure 6:
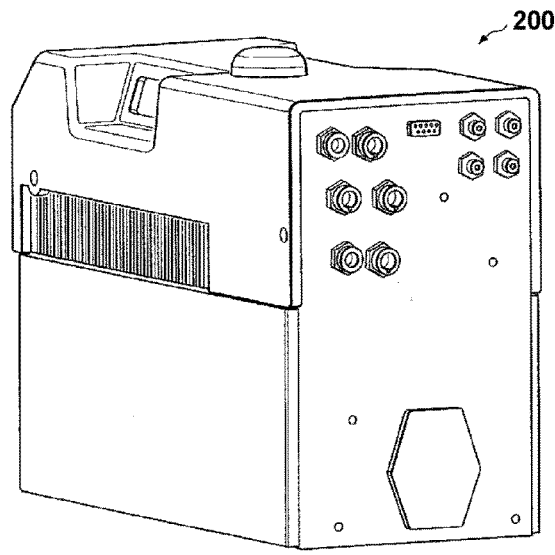
FIG. 6 is a rear perspective view of the control unit of FIG. 5.
Figure 7:
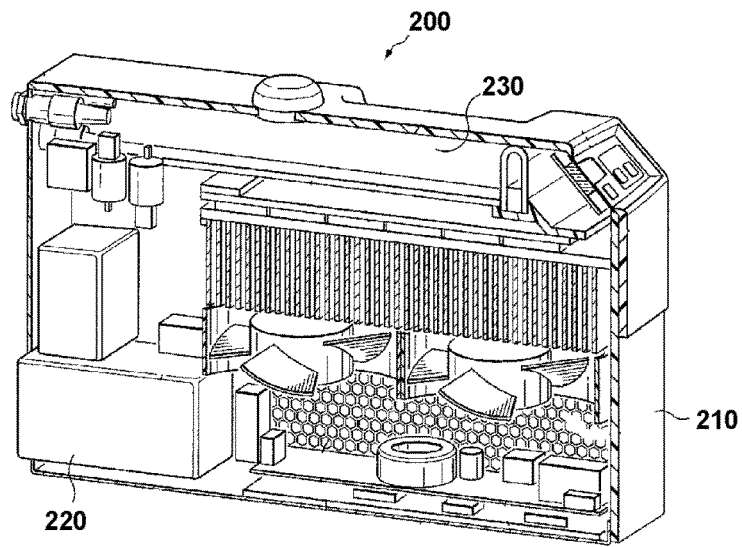
FIG. 7 is a partial cut away side perspective view of the control unit of FIG. 5, illustrating a reservoir and a power supply.
Figure 8:
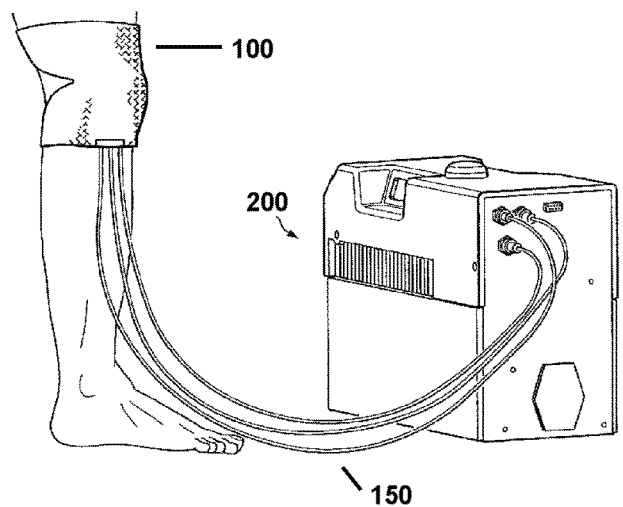
FIG. 8 is a side perspective view of a thermal compression therapy system in use on a patient's knee.
Figure 9:
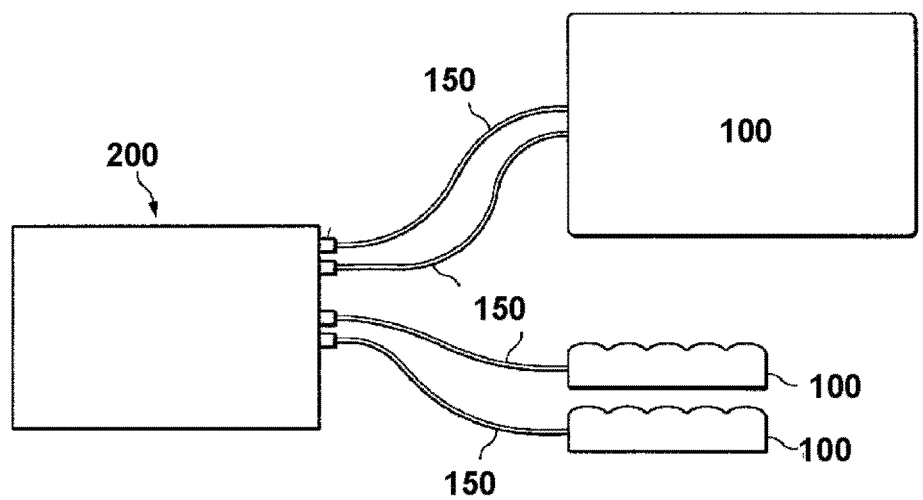
FIG. 9 is a diagrammatical view of the a thermal compression therapy system, illustrating various types of thermal compression units.
Figure 10:
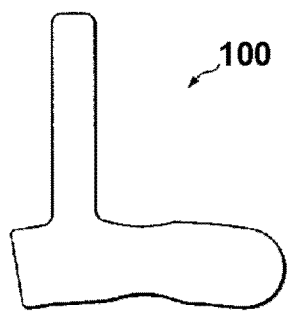
FIG. 10 is an overhead plan view of one embodiment of a thermal compression unit adapted for use on the foot of a patient.
Figure 11:
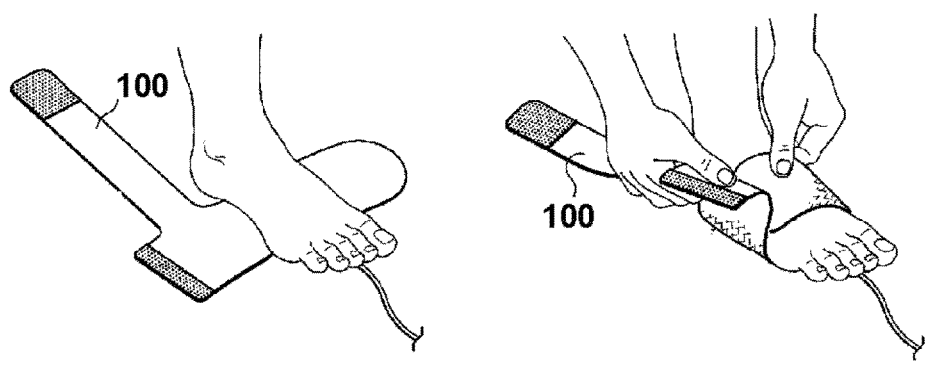
FIG. 11 is a side perspective view of the thermal compression unit of FIG. 10, showing one method of installation onto the foot of the patient.
Figure 12:
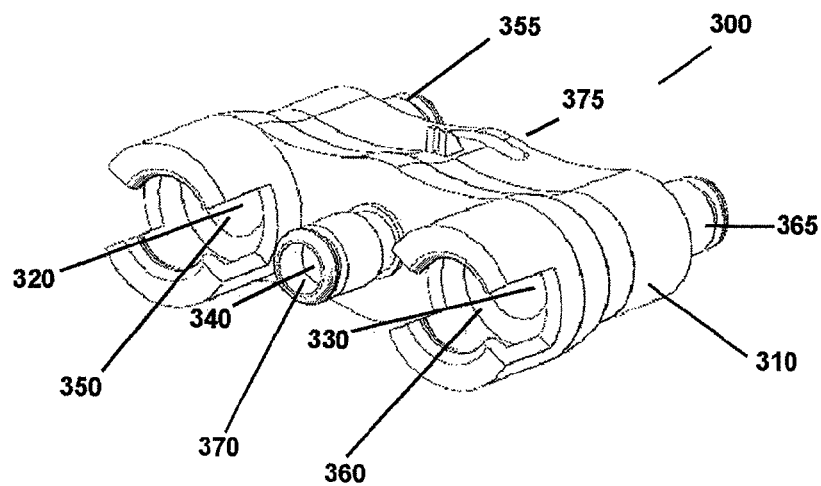
FIG. 12 is a side perspective view of a coupler for use with a thermal compression system.
Figure 13:
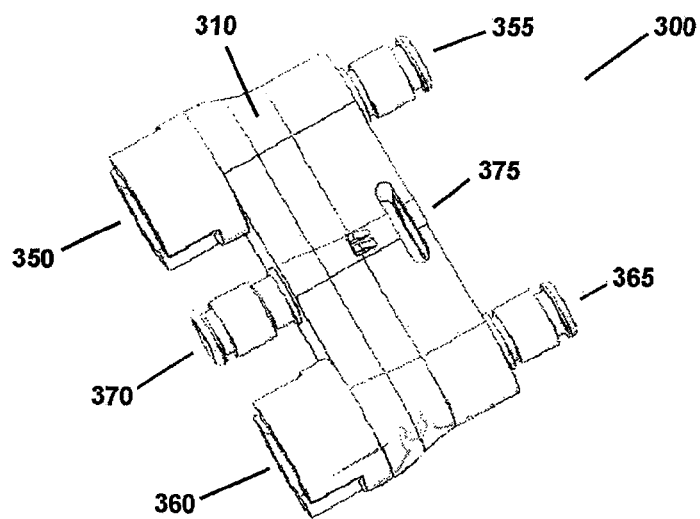
FIG. 13 is a top perspective view of the coupler of FIG. 12.

Referring now to FIGS. 1, 2, and 3, in one aspect of thermal compression unit 100, the apparatus comprises a temperature nodule 170. In this aspect, the temperature nodule 170 is a temperature sensitive structure. It can, for example, comprise aspects such as a thermometer, a thermocouple connected to a read out (typically positioned on the control unit), or a visual color-coded read out attached to a temperature sensitive structure. In another aspect, the temperature nodule comprises both a temperature-sensitive section and a display section wherein the display provides a user readable indication enabling an attending technician or professional to quickly and easily determine temperature.

In one exemplary aspect, the nodule can be disposed on the thermal compression unit 100 such that a temperature-sensitive portion of nodule is positioned proximate to the skin of a patient when the apparatus is disposed on the patient for therapy. Thus, in one aspect, the temperature-sensitive portion of nodule can also be positioned on the exterior surface of the cover that is designed to be in contact with the patient's skin. However, as can be appreciated, a read-out section can be placed on exterior surface of the cover because it is typically the surface that is visible for observation by an attendant. If necessary, wires or leads can also be used to connect any portion of temperature nodule to other devices or support structures such as a power source, a digital read out, etc. In one aspect, the system can record the temperature of the patient's skin at various intervals.

One advantage of an apparatus having a temperature nodule 170 relates to the nodule providing an accurate temperature reading on the patient's skin that generally lies under the cover 120 and overall apparatus. If a temperature in a heat therapy rises too high, there is a danger of burning the patient. Conversely, if the temperature falls too low, there is a danger of frostbite. Even when these two extremes do not occur, it is desirable to determine what the temperature of the patient's skin is as opposed to just the temperature of the fluids within the core as it is the actual skin temperature that is important in judging the effectiveness of a therapy.

Referring again to the figures, one aspect of the thermal compression unit comprises a tubing-cover section 124. The tubing-cover section 124 can be a unitary portion of the cover, for example and not meant to be limiting. A portion of the cover can be designed to extend from the main body of the cover to provide protection to the liquid tubing and the gas tubing. In operation, when the core is disposed within the interior volume 160 of the cover, the liquid tubing and gas tubing can extend from the interior volume through an aperture within cover that is designed to allow the tubings 150 to extend to the exterior region of the cover. In this way, the liquid tubing and gas tubing can make connections with supply tubings that originate in the control unit. The tubing-cover portion of the cover 120 can provide an extension of material that covers and protects the tubings from damage or contact with skin surfaces. In some aspects, the tubing-cover portion of the cover can comprise padding or protective material to cushion and protect the liquid tubing, the gas tubing, and other connecting tubings.

It is noted that the combined thermal compression unit 100 can take any desired shape to conform to specified portions of the patient's anatomy. In one aspect, as can be seen in the figures, the illustrated shape has proven useful for treatment of the human knee. In usage, the upper section 116 can wrap around an area generally above the knee joint while the lower section 114 can wrap around an area generally below the knee joint. The middle section generally follows a neck 112 or smaller cross-sectional width which allows for the upper section and lower section to readily wrap around the leg portions while also allowing the knee joint to flex. As can be appreciated, the thermal compression unit can be shaped to contour almost any extremity, including, but not limited to feet, ankles, hands, wrists, and the like. The thermal compression unit can also be configured to affix to the extremity in such a way as to permit contraction and flexion or it can be configured to restrict movement altogether.

In a further aspect of the thermal compression unit, a bridge support 180 can be provided, as a separate structure or comprised in either the core 110 or the cover. The bridge support 180 is generally positioned proximate to the area of middle section. At this area, as can be appreciated, the channels 130, 140 in the core necessarily cross through a neck 112 area of reduced cross sectional width as the fluids pass from lower section 114 to upper section 116 and vice versa. As can be appreciate, folding of the core can cause pinching of the channels, which, in turn, can cause the flow of gas or fluid to be impeded. Thus, the presence of a bridge support can prevent this from occurring. Additionally, the repetitive flexing of the patient's joint can tend to induce a fold in the flexible plastic material of the channels; this fold or bend can then lead to obstruction within the channels just as might happen when a drinking straw is folded in half. The bridge support provides a flexible but firm reinforcing material that helps prevent channels from being pinched or closed. Bridge support 180 tends to inhibit an obstructing fold from forming in channels by providing a supportive structure.

Referring again to FIGS. 1, 2, and 3 the cover is described in further detail. In one aspect, the cover 120 is constructed of a low cost material such that cover can be used as a throw away item. The cover is generally configured to closely receive the core. Thus, the cover can be a shield against contamination of the core by blood or other human discharge. The cover can comprise an impermeable surface, for example, that can be constructed of a material that prevents this kind of contamination of the core 110. However, the cover allows the function of the core to continue unimpeded by easily transmitting heating, cooling, and pressure. Thus, after a usage has taken place, the technician or nurse can throw away the cover and then reuse the core in a subsequent treatment.

Referring specifically to FIG. 3, the cover is shown having fastening straps 190 and receiving areas 192 attached to both the upper section and the lower section. In one aspect, the fastening straps 190 and receiving areas 192 can comprise a reciprocal hook and loop attachment means (e.g., VELCRO® fabric). Thus, the cover can be wrapped around a portion of the patient's body, and then the fastening straps and receiving areas can be brought into contact. In this manner the cover can be securely attached to the patient. The cover can also be secured in this manner when the core is disposed within cover.

As has been previously mentioned, the core can be assembled with the cover by passing the core through the opening 126 of the cover and into the interior volume of the cover. The opening 126 can comprise a closure means 128 for securing the opening in a closed position to securely hold the core within interior volume. In one aspect, the closure means 128 comprises a hook and loop reciprocal attachment fabric such as VELCRO® fabric; however, other aspects can use other known kinds of fasteners such as zippers, buttons, clips and the like.

In one aspect, a control unit is presented that is adapted to provide the thermally controlled fluid and compressed gas for multiple therapeutic modalities. The control unit for providing these selective features can be enclosed within a single chassis design capable of providing the described modalities. In another aspect, the control unit can comprise a separate temperature control unit and a pressure control unit, or it can comprise a single control unit 200 housing both modalities. This selective versatility provides financial and manufacturing incentives in that the simple design selectively can provide an industrial, medical, or electro-optic version that produces only thermally controlled liquid, such as co-liquid for cooling industrial equipment, in a configuration adaptable for other applications.

In another aspect, thermal therapy can be afforded to a patient to reduce swelling and edema while, in conjunction with the DVT prophylaxis, preventing blood from pooling in lower body extremities. This is particularly important after surgery when anesthesia has been involved. It is well known that anesthetics often tend to reduce the wall strength of veins and, if not otherwise treated, appropriate venous pumping can not be afforded allowing for blood pooling in clots.

In an exemplary aspect, the control unit can be provided for thermal and compression therapy. The control unit can be adapted to be coupled to thermal and compression elements to be applied to a patient. In this particular aspect, the control unit can comprise a filter 210 for filtering the compressed gas. In one aspect, the filter can be removable. In another aspect, the filter can comprise a gas-filtering substance, such as woven netting, that can be attached by VELCRO fasteners or the like outwardly of a perforated metal grate to allow for the low-pressure drawing of gas therethrough. This would allow cooling of components inside the control unit 200. In yet another aspect, the control unit 200 can comprise one or more fans to force gas across one or more heat transfer assemblies (HTA).

In one aspect, a HTA can be disposed beneath a fluid reservoir 230. The reservoir 230 can be configured to store liquid to be pumped into the first channel 130 via a fluid connector. In another aspect, the fluid connector can be configured to be coupled to one or more cores. As can be appreciated, in some aspects, a dual-fan arrangement can be used. The fans can, for instance, be positioned to push and/or pull gas into the interior of the control unit to distribution about the electronic components so that the gas flow is both quiet and at a rate allowing initial electronic cooling and then being available to be pushed into sections of the control unit where most heat dissipation is needed.

In yet another aspect, a power supply 220 can be disposed internally within the control unit, or it can be external thereto. In various exemplary aspects, the power supply 220 can be a 500 Watt power supply. In some aspects, additional power supplies can also be used to power various components. For example, in addition to a 500 Watt power supply, a 65 Watt power supply can be used for components requiring less power. In some aspects, the power supplies are adapted to receive a plurality of inputs so the control unit can be used in a plurality of countries without requiring substantial reconfiguration.

A fluid pump, for example, can also be comprised within the control unit for collecting fluid from a reservoir that has been thermally controlled by the HTA. Thermal electric cooling devices (TEC) can also be used. In one aspect, the TECs a positioned between a heat sink and a thermal transfer plate in a manner to provide the requisite thermal control of the fluid within the reservoir.

In one aspect, the control unit 200 for providing these selective features can be enclosed within a single chassis design capable of providing the described modalities. This selective versatility provides financial and manufacturing incentives in that the simple design selectively can provide an industrial, medical, or electro-optic version that produces only thermally controlled liquid, such as co-liquid for cooling industrial equipment, in a configuration adaptable for other applications. In another aspect, the size of the reservoir has been reduced relative to a number of earlier models of thermoelectric cooler (TEC) systems such that only around 175 Watts can be needed compared to 205 Watts for typical earlier systems. As such, the control unit can be configurable with TEC assemblies maximizing efficiency. With regard to a medical modality, thermal therapy can be afforded to a patient to reduce swelling and edema while, in conjunction with the DVT prophylaxis, preventing blood from pooling in lower body extremities. This is particularly important after surgery when anesthesia has been involved. It is well known that anesthetics often tend to reduce the wall strength of veins and, if not otherwise treated, appropriate venous pumping may not be afforded allowing for blood pooling in clots.

In one aspect, a plurality of gas connectors and fluid connectors can be used to provide thermally conditioned heat-transfer fluid to a plurality of thermal therapy devices and to provide pressurized gas to a plurality of compression therapy devices and DVT compression devices. In some aspects, fluid connectors are provided in to facilitate circulation of fluid in a closed loop in an outward bound and an inward bound flow of fluid to and from the fluid reservoir 230 for thermal control. In some aspects, a single compression therapy device can be coupled to a plurality of gas connectors and the control unit can be programmed accordingly to provide compressed gas in a sequenced manner to a plurality of cores in the compression therapy device. For example, a first core can be inflated, followed by the inflation of a second core, which is then followed by the inflation of a third core, and so on. The first core can be deflated before or after the second core is inflated, or the first core can remain inflated until all the cores are inflated.

In a further exemplary aspect, the system comprises a coupler 300 configured to selectively connect the first channel 130 to the liquid source and the second channel 140 to the compressed gas source. In this aspect, the coupler 300 comprises a body 310 defining a first interior pathway 320 and a second interior pathway 330. Each pathway has an inlet and an outlet. The inlet 350 for the first interior pathway 320 can be configured to selectively couple with the first channel 130, the outlet 355 of the first interior pathway 320 can be configured to selectively couple with the liquid source, the inlet 360 of the second interior pathway 330 can be configured to selectively couple with the second channel 140, and the outlet 365 of the second interior pathway 330 can be configured to selectively couple with the compressed gas source.

In another aspect, the body 310 of the coupler further defines a third interior pathway 340 having an inlet 370 and an outlet 375. In this aspect, the inlet 350 of the first interior pathway can be configured to selectively couple with a first port 132 of the first channel 130 and the inlet 370 of the third interior pathway 330 can be configured to selectively couple with a second port 134 of the first channel 130. Additionally, the outlet 375 of the third interior pathway 340 can be configured to selectively couple with the liquid source.

As one skilled in the art will appreciate, some or all of the inlets can comprise a male or female quick disconnect coupling. Likewise, the respective outlets can comprise a complimentary quick disconnect coupling. In one exemplary aspect, the inlets for the first interior pathway 320 and the third interior pathway comprise a female quick disconnect coupling, and the outlets for the first interior pathway comprise a male quick disconnect coupling. Similarly, in this aspect, the inlet for the second interior pathway comprises a male quick disconnect coupling, and the outlet for the second interior pathway comprises a female quick disconnect coupling.

In some aspects, the cores 110 are pressurized in accordance with the medical modality described herein and the parameters are set by the programming within the control boards of the control unit. Additionally, an RS232 connector for data communication with the control unit may be provided. In other aspects, other connections can be used such as, for example, a USB connection, or a wireless connection.

In various aspects, the control unit 200 can be used to initiate and control different sequencing patterns, times, and pressures, depending on the type of treatment desired. Various aspects allow a plurality of parameters to be specified by a user, such as, for example, the inflated pressure, the deflated pressure, the rate of inflation, the inflation-hold time, and the cycle time. For example, in one treatment modality, the control unit 200 can provide compressed gas to inflate a DVT compression device for 3-20 seconds when the DVT compression device is disposed on a calf. Thus, the control unit can be configured to provide a series of timed pulses of compressed gas. The time period of the pulse can be more or less depending on the part of the body being treated. For example, a pulse width of around 0.3 seconds can be desirable for a foot. Similarly, the inflation times may vary depending on whether DVT compression devices located on both right and left extremities are being inflated simultaneously or whether the inflation is being alternated between the devices. For example, an inflation period of 18 seconds may be desirable for simultaneous inflation whereas an inflation period of 8 seconds may be desirable when the inflation is being alternated. Similarly, when DVT compression devices are disposed around a patient's right and left feet, in some situations it may be desirable to have a wide pulse width on the order of 9 seconds whereas in other situations it may be desirable to have a narrow pulse width on the order of 0.3 seconds. In addition, it may be desirable to vary the cycle times in between DVT pulses. For example, in some aspects, a cycle time of 20 seconds in between DVT pulses may be desirable. Similarly, in some aspects, it may be desirable to completely deflate the DVT compression devices in between inflations while in other aspects, it may be desirable to keep the DVT compression devices partially inflated. As can be seen from the above examples, it would be desirable to have a programmable control unit that can be adapted to provide DVT compression at user-specified parameters.

In another aspect, a method for providing a combined DVT and compression therapy to a patient is disclosed. The method comprises the steps of providing a control unit configured to condition heat transfer fluid and to selectively provide a compressed gas; providing a thermal compression device that is mountable to a select portion of the patient; and programming the control unit 200 to supply heat transfer fluid to the thermal compression device within a first predetermined temperature range and to supply compressed gas to the thermal compression device within a first predetermined pressure range. In this aspect, the thermal compression device is in operative communication with the control unit.

As described in the various treatment modalities herein, the control unit can be programmed to supply the heat transfer fluid and the compressed gas to the thermal compression device in various manners. In fact, the control unit can supply more than one thermal compression device. In one exemplary aspect, the heat transfer fluid and the compressed gas are supplied to the thermal compression device sequentially. In another aspect, the sequential supply of the heat transfer fluid and the compressed gas is repeated for a predetermined number of treatment applications. In still another aspect, the supply of the heat transfer fluid at least partially overlaps in time sequence with the supply of the compressed gas. As need for the therapy regimen, the heat transfer fluid and the compressed gas can also be supplied to the thermal compression device substantially simultaneously. The system can be adapted to the patient in multiple modalities regulated by the control unit.

As described herein, the control unit can provide thermal conditioning of the heat transfer fluid to both cool and heat the thermal transfer fluid, depending on the therapy desired. In one aspect, the heat transfer fluid is conditioned to a temperature of between about 37° F. and about 105° F. In a similar manner, the control unit can provide compressed gas at pressures necessary for the particular therapy desired. In one aspect, the control unit 200 can provide compressed gas to the thermal compression unit 100 at a pressure at or below about 120 mm Hg. In various other exemplary aspects, the control unit can provide compressed gas at pressure at or below 100 mm Hg, at or below 80 mm Hg, at or below 60 mm Hg, at or below 40 mm Hg, or at or below 35 mm Hg. In still another aspect, the control unit can provide compressed gas at a pressure of about 25 mm Hg.

In another aspect, the control unit can be programmed to supply the heat transfer fluid to the thermal compression device for a predetermined heating time, depending upon the therapy desired. In one aspect, the predetermined heating time is between about 5 minutes and about 25 minutes. In still another aspect, the control unit can be programmed to supply the compressed gas to the thermal compression device for a predetermined compression time. As can be appreciated, the method can also comprise varying the temperature of heat transfer fluid supplied to the thermal compression unit and/or varying the pressure of compressed gas provided to the thermal compression unit. In still another aspect, the method can comprise supplying compressed gas to the thermal compression device until it reaches a predetermined pressure and, then, allowing the thermal compression device to deflate and repeating, as necessary. In one aspect, the predetermined pressure is 35 mm Hg.

In another exemplary aspect, the method described herein can comprise using the thermal compression unit on one or more body parts of the patient. For example, and not meant to be limiting, them method can comprise using the thermal compression unit 100 on a knee of the patient, a calf of a patient, a foot of a patient, and the like.

As mentioned herein, the method can also comprise using a plurality of thermal compression devices, as needed for the desired therapy. As such, the control unit can be programmed to supply heat transfer fluid to the second thermal compression device within a second predetermined temperature range and to supply compressed gas to the second thermal compression device within a second predetermined pressure range. In one aspect of the method, the first predetermined temperature range can be substantially the same as the second predetermined temperature range. In another aspect of the method, the first predetermined pressure range can be substantially the same as the second predetermined pressure range. As one can appreciate, the pressures and temperatures of the first and second thermal compression devices can also be varied.

In one embodiment, the system for a DVT and compression therapy system comprises a control unit comprising a processing system as described herein. Specifically, the processing system of the control unit can comprise a memory, configured for storing a software program, a first predetermined temperature range, a first predetermined pressure range, and at least one application protocol, and a processor, coupled to the memory.

In one aspect, the processor can be configured for executing the software program, selectively directing the supply of a heat transfer fluid at a temperature selected from the first predetermined temperature range, selectively directing the supply of a compressed gas at a pressure selected from the first predetermined pressure range; and selectively directing the supply of the heat transfer fluid and the compressed gas in accordance with an application protocol selected from the at least one application protocol. In another aspect, the processor can be configured for directing the steps of the methods described herein.

Although several aspects of the invention have been disclosed in the foregoing specification, it is understood by those skilled in the art that many modifications and other aspects of the invention will come to mind to which the invention pertains, having the benefit of the teaching presented in the foregoing description and associated drawings. It is thus understood that the invention is not limited to the specific aspects disclosed hereinabove, and that many modifications and other aspects are intended to be comprised within the scope of the appended claims. Moreover, although specific terms are employed herein, as well as in the claims which follow, they are used only in a generic and descriptive sense, and not for the purposes of limiting the described invention, nor the claims which follow.

What is claimed is:

1. A system for addressing deep-vein-thrombosis (DVT) in a patient utilizing compression therapy, the system comprising:
   a control unit adapted to thermally condition a heat-transfer liquid to a predetermined temperature and to provide compressed gas at one or more predetermined pressures;
   a thermal therapy pad adapted for the flow of the heat-transfer liquid there through and being coupled to the control unit;
   a compression therapy device having a bladder and adapted to be disposed outwardly of the thermal therapy pad and being coupled to the control unit for receiving at least a portion of the compressed gas to fill the bladder and adapted to compress the thermal therapy pad against a first portion of a first extremity of the patient;
   a first DVT compression device coupled to the control unit and adapted to receive a first pulse of compressed gas from the control unit, the first DVT compression device adapted for securement to and compression of a second portion of the first extremity of the patient;
   a second DVT compression device coupled to the control unit and adapted to receive a second pulse of compressed gas from the control unit, the second DVT compression device adapted for securement to and compression of a portion of a second extremity of the patient;
   wherein the control unit automatically directs the first pulse only when the compressed gas is not being applied to the compression therapy device.

2. The system of claim 1, wherein the thermal therapy pad and the compression therapy device are integrated into a single device.

3. The system of claim 1, wherein compressed gas is provided to the first DVT compression device during the first pulse for a user-specified length of time and compressed gas is provided to the second DVT compression device during the second pulse for a user-specified length of time.

4. The system of claim 1, wherein the control unit is adapted to provide the compressed gas to the compression therapy device, the first DVT compression device, and the second DVT compression device at one or more user-specified pressures.

5. The system of claim 1, wherein the control unit is adapted to cycle through the following:
   provide a pulse of compressed gas to a first bladder of the compression therapy device;
   provide a pulse of compressed as to a second bladder of the compression therapy device;
   provide a pulse of compressed gas to a third bladder of the compression therapy device.

6. A method for addressing aspects of deep vein thrombosis (DVT) in a patient utilizing compression applied to the patient, the method comprising:
   providing a control unit adapted to thermally condition a heat transfer fluid to a temperature within a range of about 37° F. and about 105° F., and adapted to provide compressed gas at a pressure of at least 25 mmHg greater than an ambient atmospheric pressure;
   providing a thermal compression device for securement to the patient and adapted to receive at least a portion of the heat transfer fluid and at least a portion of the compressed gas from the control unit;
   providing first and second DVT compression devices for securement to the patient, each being adapted to receive at least a portion of the compressed gas from the control unit;
   coupling the thermal compression device, the first DVT compression device, and the second DVT compression device to the control unit; and
   programming the control unit to automatically coordinate the distribution of the compressed gas between the thermal compression device and the first and the second DVT compression devices so that the thermal compression device does not receive compressed gas at the same time the first DVT compression device receives compressed gas.

7. The method of claim 6, wherein the first and the second DVT compression devices are secured to select appendages of the patient.

8. The method of claim 6, further comprising monitoring a condition of the patient in at least partial dependence on the compressed gas being provided to the thermal compression device.

9. The method of claim 8, wherein the compressed gas provided to the thermal compression device is varied based on the condition monitored.

10. The method of claim 6, wherein the heat transfer fluid is heated from about 49° F. to about 105° F. and applied to a skin area of the patient.

11. The method of claim 6, wherein the heat transfer fluid is cooled from about 105° F. to about 49° F. and applied to a skin area of the patient.

12. The method of claim 6, wherein the heat transfer fluid is cooled from an ambient temperature of about 77° F. to a temperature of about 37° F. within a 90 minute period.

13. The method of claim 6, wherein the control unit is adapted to provide the compressed gas at a pressure in the range of about 0 to about 120 mm Hg.

14. A method for addressing aspects of deep vein thrombosis (DVT) in a patient utilizing compression applied to the patient, the method comprising:
providing a plurality of compression devices for securement to the patient and adapted to receive at least a portion of compressed gas from a control unit, wherein at least one of the compression devices is a thermal compressing device, and wherein the plurality of compression devices includes a first DVT compression device and a second DVT compression device for securement to the patient, each being adapted to receive at least a portion of the compressed gas from the control unit;
coupling the plurality compression device to the control unit;
programming the control unit to automatically coordinate the distribution of the compressed gas to the compression devices such that only one compression device is compressed at a time and the compression alternates between compression devices; and
programming the control unit to automatically coordinate the distribution of the compressed as between the thermal compression device and the first DVT compression device and the second DVT compression device, so that the thermal compression device does not receive compressed gas at the same time the first DVT compression device receives compressed gas.

15. The method of claim 14, further comprising coupling the first DVT compression device and the second DVT compression device to the control unit.

16. A method for addressing aspects of deep vein thrombosis (DVT) in a patient utilizing compression applied to the patient, the method comprising:
automatically coordinating, by the control unit, distribution of compressed gas to compression devices such that only one compression device is compressed at a time and the compression alternates between the compression devices; and
automatically coordinating, by the control unit, a sequence of distribution of the compressed gas and a heat transfer fluid to a thermal compression device,
wherein a plurality of compression devices are secured to the patient,
wherein the plurality of compression devices are adapted to receive at least a portion of the compressed gas from the control unit, and
wherein the plurality of compression devices are coupled to the control unit.

17. The method of claim 16, wherein the step of programming further comprises coordinating the sequence of the distribution of the compressed gas and the heat transfer fluid to the thermal compression device.

18. A method for addressing aspects of deep vein thrombosis (DVT) in a patient utilizing compression applied to the patient, the method comprising:
automatically coordinating, by a control unit, distribution of compressed gas to compression devices such that only one compression device is compressed at a time and the compression alternates between the compression devices; and
automatically coordinating, by the control unit, distribution of a heat transfer fluid to a thermal compression device,
wherein a plurality of compression devices are secured to the patient,
wherein the plurality of compression devices are adapted to receive at least a portion of the compressed gas from the control unit, and
wherein the plurality of compression devices are coupled to the control unit.

* * * * *

UNITED STATES PATENT AND TRADEMARK OFFICE
CERTIFICATE OF CORRECTION

| | | |
|---|---|---|
| PATENT NO. | : 8,485,995 B1 | Page 1 of 1 |
| APPLICATION NO. | : 12/501258 | |
| DATED | : July 16, 2013 | |
| INVENTOR(S) | : Gregory Brian Maxon-Maldonado | |

It is certified that error appears in the above-identified patent and that said Letters Patent is hereby corrected as shown below:

In the Claims:

Col. 13, line 27, please delete "compressing" and insert therefor --compression--.

Signed and Sealed this
Third Day of September, 2013

Teresa Stanek Rea
*Acting Director of the United States Patent and Trademark Office*